(12) United States Patent
Duriez et al.

(10) Patent No.: US 7,232,548 B2
(45) Date of Patent: Jun. 19, 2007

(54) TRANSPORT DEVICE FOR ANALYZING HYDROCARBON-CONTAINING CONSTITUENTS

(75) Inventors: Gilbert Duriez, Rueil-Malmaison (FR); Bernard Dewimille, Corbeil Essone (FR)

(73) Assignee: Institut Francais du Petrole, Rueil-Malmaison Cedex (FR)

( * ) Notice: Subject to any disclaimer, the term of this patent is extended or adjusted under 35 U.S.C. 154(b) by 997 days.

(21) Appl. No.: 09/887,066

(22) Filed: Jun. 25, 2001

(65) Prior Publication Data
US 2002/0001543 A1 Jan. 3, 2002

(30) Foreign Application Priority Data
Jun. 28, 2000 (FR) .................................. 00 08445

(51) Int. Cl.
*G01N 30/00* (2006.01)
(52) U.S. Cl. ........................ 422/83; 422/68.1; 436/139; 436/180
(58) Field of Classification Search ................ 422/83, 422/88, 68.1, 78; 436/9, 139, 180
See application file for complete search history.

(56) References Cited

U.S. PATENT DOCUMENTS

| 3,615,235 A | 10/1971 | Hrdina |
| 4,692,698 A | 9/1987 | Lewis |
| 5,090,256 A * | 2/1992 | Issenmann ............... 73/863.23 |
| 5,566,720 A * | 10/1996 | Cheney et al. .............. 138/137 |
| 5,691,809 A | 11/1997 | Tackett |
| 5,749,942 A * | 5/1998 | Mattis et al. .................. 95/46 |

FOREIGN PATENT DOCUMENTS

| GB | 1569984 | 6/1980 |
| GB | 2260812 | 4/1993 |

\* cited by examiner

Primary Examiner—Jill Warden
Assistant Examiner—Samuel P. Siefke
(74) Attorney, Agent, or Firm—Antonelli, Terry, Stout & Kraus, LLP.

(57) ABSTRACT

An analysis and/or measuring device includes means for extracting, in the gaseous form, hydrocarbons contained in a liquid fluid, means for transporting said extracted gases, and means intended for analysis and measurement on these extracted gases. The transport means include a tubular line having an inner tube made from at least one of the following plastics or from mixtures thereof: fluoropolymers, such as PTFE, fluoroelastomers, such as THV, and Ketone polymer type elastomers, such as PEEK.

15 Claims, 7 Drawing Sheets

TRANSPORT DEVICE FOR ANALYZING HYDROCARBON-CONTAINING CONSTITUENTS

FIELD OF THE INVENTION

The present invention mainly relates to the sphere of analysis and measurement of gaseous and/or liquid constituents that can be contained in drilling fluids. The invention is advantageously applied for mud logging operations, which consist in measuring while drilling, notably the drilling fluid backflow.

BACKGROUND OF THE INVENTION

Various documents, notably document U.S. Pat. No. 5,090,256, describe methods of extracting gaseous constituents contained in drilling fluids so as to detect the presence of said constituents in the reservoir rocks crossed through. The measuring principle consists in continuously taking a certain volume of drilling fluid in order to <<degas>> it in a suitable device. The gases extracted from the fluid sample are then transported to a measuring cab located at a distance from the wellhead. The transport line is generally a tube that is several ten meters long. The transported gases are then analysed by chromatography in the cab.

In order to increase the quantification precision and to extend the possibility of carrying out measurements on hydrocarbons, tests have shown that conventional devices are not efficient enough, in particular for hydrocarbon-containing constituents above C4.

The object of the present invention is to provide an analysis device and method allowing to prevent or at least to limit retention, adsorption and absorption phenomena that lead to erroneous qualitative analysis results and make quantification difficult or even impossible, thus causing analysis delay phenomena that can lead to interpretation errors concerning the zones crossed by the borehole. Furthermore, these adsorption and absorption effects can be followed by non-quantifiable salting-out phenomena that make correlation of the measurements performed difficult according to the borehole depth.

SUMMARY OF THE INVENTION

The present invention thus relates to a continuous analysis device comprising means for extracting, in the gaseous form, hydrocarbons contained in a liquid fluid, means for transporting the extracted gases, and means intended for analysis and measurement on these extracted gases. According to the invention, the transport means include a tubular line comprising an inner tube made from at least one of the following plastics, or from mixtures thereof:
fluoropolymers such as PTFE (polytetrafluoroethylene), FEP (tetrafluoroethene-perfluoroprene copolymer), PVDF (polyvinylidene fluoride), ETFE (tetrafluoroethylene-ethylene copolymer), ETFCE (ethylene-trifluorochlorethylene copolymer), PCTFE (polychlorotrifluoroethylene), PFA (perfluoroalkoxyalkane),
fluoroelastomers such as VITON (registered trademark of Dupont de Nemours) (hexafluoropropylene-vinylidene fluoride copolymer), or hexafluoropropylene-vinylidene fluoride-tetrafluoropropylene THV terpolymers, or tetrafluoroethylene-hexafluoropropylene-treated vinylidene fluoride,
Ketone polymer type elastomers such as PEEK (polyetherether ketone), but also PEKK, PAEK, PEK, aliphatic polyketone.

In a preferred variant, the transport line can comprise a tube made of THV or PTFE, externally protected by at least one other sheath.

The thickness of the inner tube according to the invention can range between 0.1 and 0.5 mm. These plastics are relatively costly but efficient even with a limited thickness.

The inside diameter of the inner tube can range between 3 and 12 mm, preferably between 6 and 10 mm.

BRIEF DESCRIPTION OF THE DRAWINGS

Other features and advantages of the present invention will be clear from reading the description hereafter of tests illustrated by the accompanying drawings, wherein.

DETAILED DESCRIPTION

Figure 1:
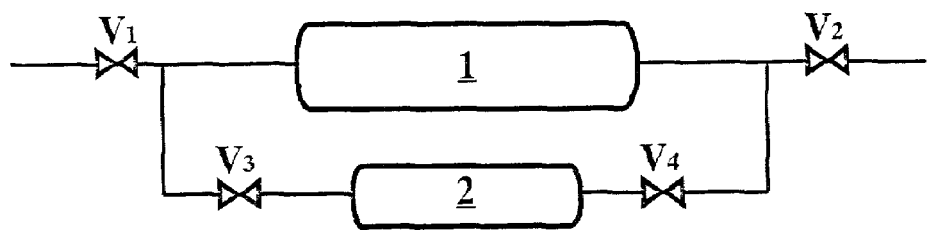
FIGS. 1, 2, 3 and 8 show testing means.

The sample injected is prepared by means of the system shown in FIG. 1.

This device consists of two glass bulbs 1 and 2 which can each be isolated by two valves V3 and V4. Valves V1 and V2 isolate both bulbs.

Bulb 2 is filled with the liquid hydrocarbon(s). After closing valves V3 and V4, the rest of the assembly is evacuated. The other part is then saturated with the hydrocarbon gas or gases. The device is isolated by closing valves V1 and V2. Valves V3 and V4 are opened so as to admix the gas with the liquid (reinforced by gentle stirring). After a moment, and after complete draining of the liquid from bulb 1, valves V3 and V4 are closed. A mixture of light hydrocarbon saturated with heavy hydrocarbon, ready to be injected, is obtained (the volume is about 35 cc). Binary gas mixtures can also be obtained with this device. The device has allowed to obtain a mixture of toluene-saturated methane (2% concentration approximately).

Figure 2:
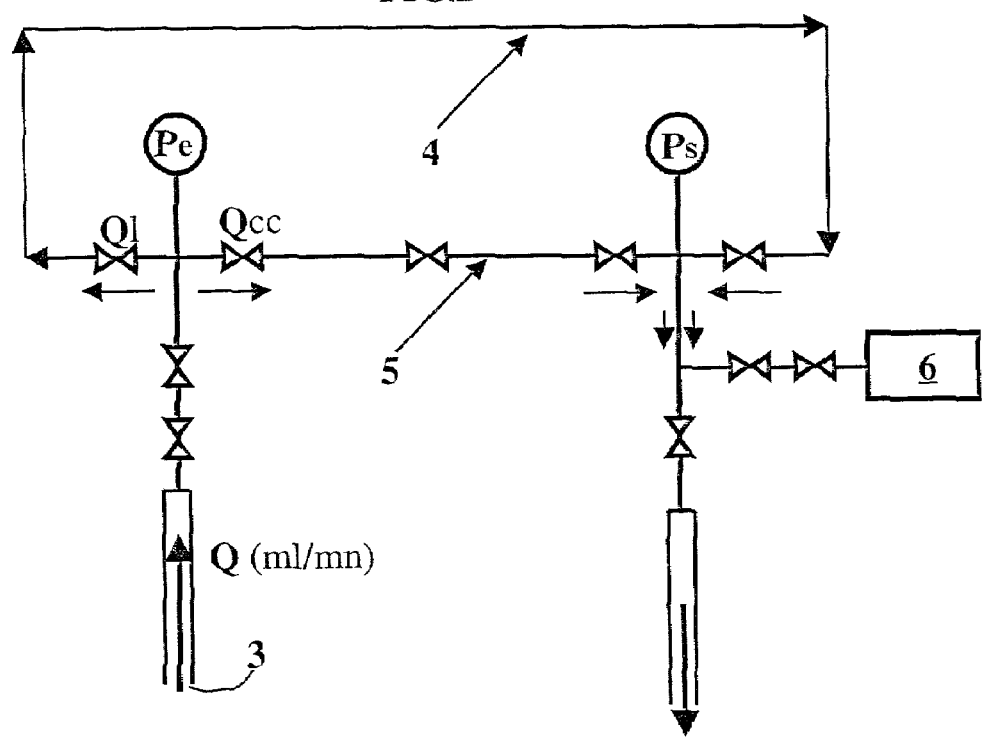

FIG. 2 shows a testing assembly consisting of a ¼ stainless steel tube allowing, upon injection of a gaseous sample through inlet 3, to separate the sample into two parts Q1 and Qcc, respectively injected into line 4 to be tested and into stainless steel short-circuit line 5. Various valves and regulators complete the circuit. Reference number 6 refers to the analysis means, a mass spectrograph for example.

Short-circuit line 5 allows the sample to be analysed more quickly in the spectrograph.

Line 4 consists of a variable tube length made of various tested materials.

It is assumed that the <<short-circuit>> part is practically free of constituent losses, and the signal resulting from measurement of the mixture coming from this section, which appears earlier on the spectrograph than the signal resulting from flow Q1 through line 4, can serve as a reference.

Figure 3:
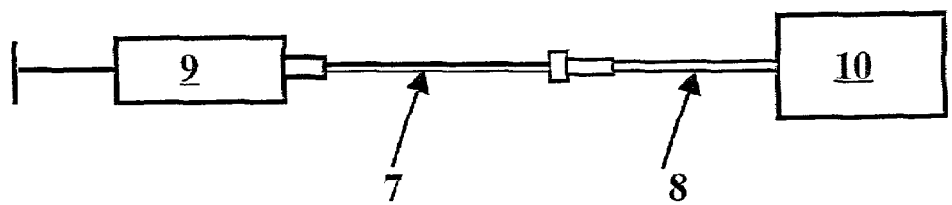

FIG. 3 shows a simplified assembly allowing to test a certain number of tubes made of different materials. Test tube 7 is fastened to a 1.5-m long tube 8 made of PEEK that is 250 µm in inside diameter. In order to obtain comparative test conditions, a mass spectrometer 10 connected to capillary tube 8 made of PEEK, assumed to be loss-free, is used. A syringe 9 allows the constituent sample to be injected.

The injected mixture consists of:
1 cc vapours taken from the gas overhead of a toluene bottle,
9 cc methane.

Injection is performed by suction of a small part of this mixture at the air inlet of the assembly.

By means of this assembly, several 50-cm long tubes made of different materials are tested in order to determine which one, or ones, correctly carries the heavier compounds, such as toluene. A glass tube, a treated glass tube, a polyethylene tube, a rubber <<vacuum>> tube and a thin THV tube were tested. The treated (chemically inerted) glass is bathed in dimethyldichlorosilane. After several flushing operations with anhydrous methanol, the tube is dried at a temperature of about 95° C.

The quantities of compounds salted out after injecting pure C1 were measured.

Two product families result from these tests:
a first family comprises glass, treated glass and THV, where adsorption is low. The results obtained with THV are less interesting, but the section of the THV tube (ID=7.3 mm, instead of 4 mm for the other tubes) being greater than that of the other tubes, it attenuates the quality of the responses as a result of the reduction in the rate of circulation of the effluents.

The results obtained with the (rubber) vacuum tube and the polyethylene tube are very negative. These tubes practically absorb completely the hydrocarbons without salting out after methane washing.

These tests have led to testing plastic tubes made of THV, PTFE and PEEK which all have properties of very low hydrocarbon permeability, even with limited thicknesses of the order of some tenths of a millimeter.

Figure 4:
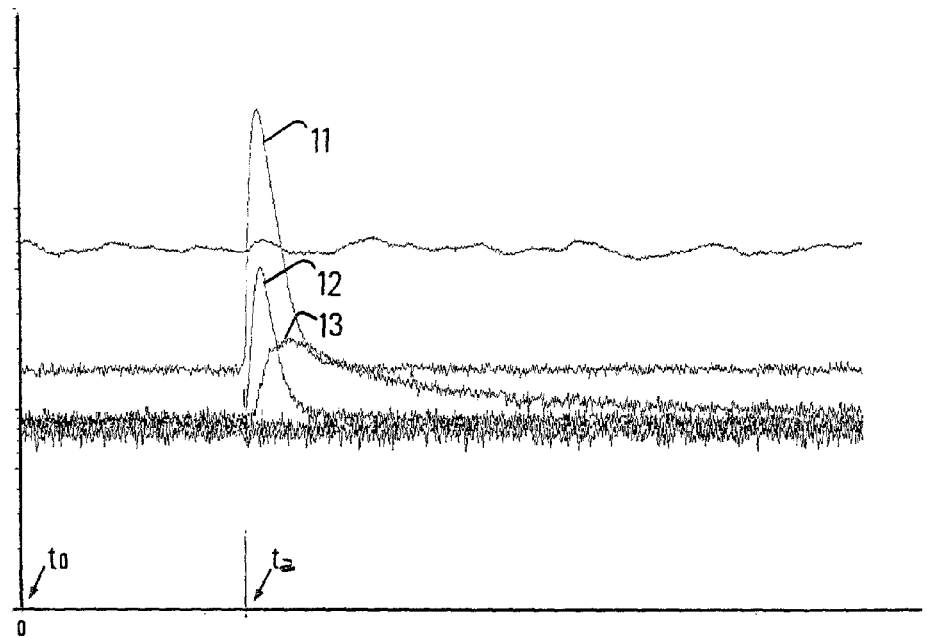
FIGS. 4, 5a, 5b, 6a, 6b, 7, 9, 10, 12 and 13 show the measurements performed by means of a spectrograph.

FIG. 4 shows the injection of a mixture of gaseous hydrocarbons into a polyvinyl chloride tube, by means of the assembly shown in FIG. 2. The PVC tube is 50 m long and 10 mm in diameter. The mixture injected at 3 comprises C1, C5 and benzene.

Injection is carried out at the time t0, its arrival is detected by the spectrograph at the time ta. Peak 11 corresponds to C1, peak 12 to C5 and peak 13 to benzene. The homothetic shape of peaks 11 and 12 shows that the transport of C1 and C5 is regular and substantially complete. On the other hand, the trailing shape of signal 13 relative to the benzene shows a poor transport.

Figure 5A:
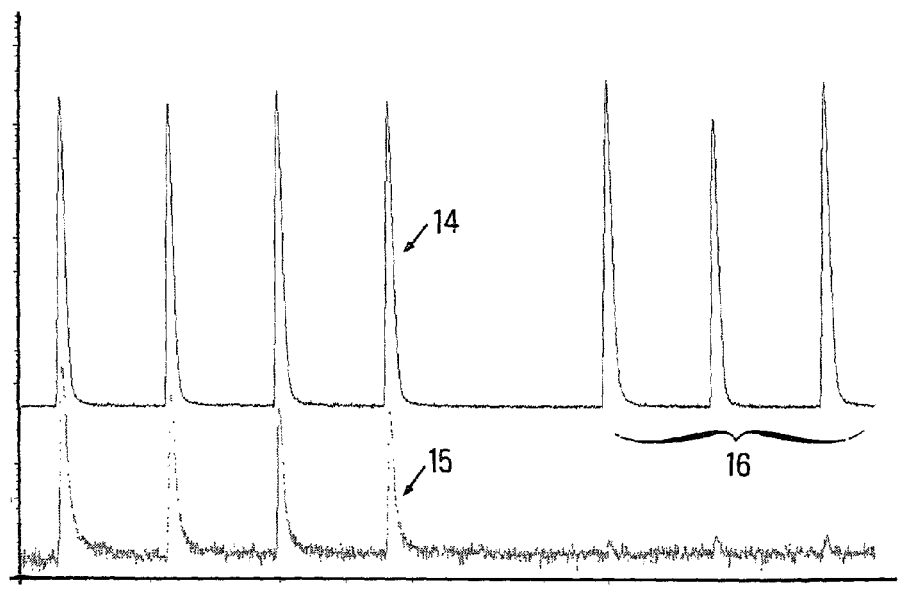
Figure 5B:
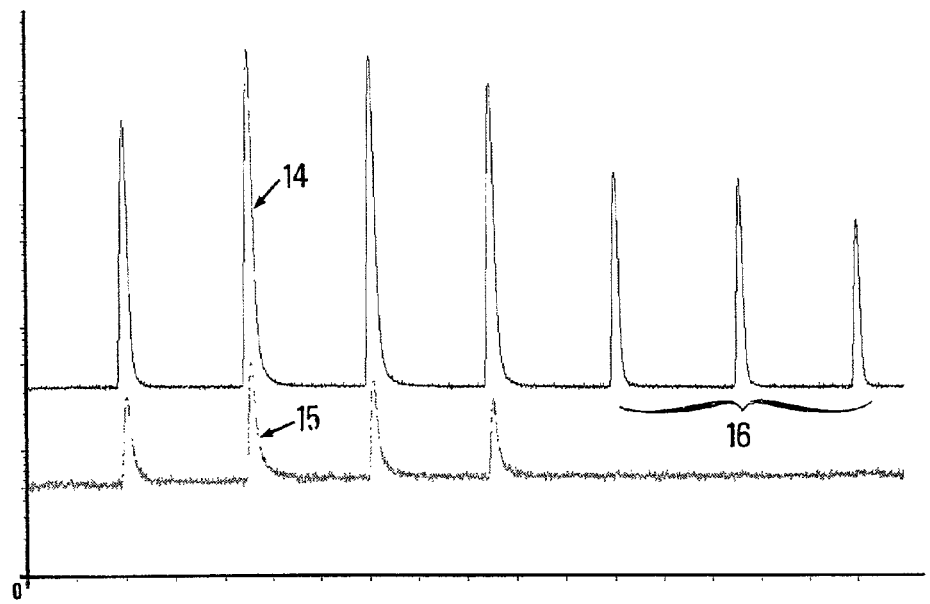

FIGS. 5a and 5b show the results of tests carried out by means of the assembly of FIG. 2, with a 50-m long THV tube that is 7.3 mm in inside diameter, with a thickness below 0.5 mm. The mixture injected comprises C1 and C7 with a concentration corresponding to a C7/C1 molar ratio of 0.4%.

The conditions of the test described in FIG. 5a are as follows: Q=93 ml/min, Ps=20 mb, Pe=34 mb. The test shown in FIG. 5b differs from the previous one in an injection rate of 21 ml/min. These two tests allow to compare the results for different transit times.

Peaks 14 and 15 respectively represent the responses upon arrival of C1 and C7.

The comparable shape of the peaks and their regularity show an excellent transport in a THV tube. The C1 peaks in zones 16 of FIGS. 5a and 5b result from washing of the THV line with pure C1. The absence of C7 peaks in these zones shows that no C7 is adsorbed in the THV line.

A 100-m long polyethylene tube that is 10 mm in inside diameter and 12 mm in outside diameter is tested with the same means as those used for testing the THV tube, and from an identical injected sample.

Figure 6A:
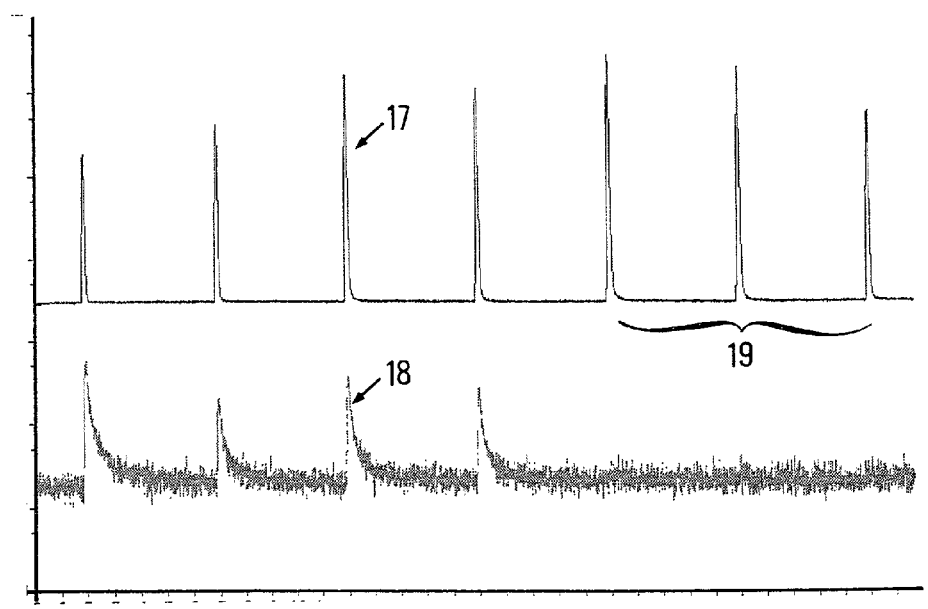
Figure 6B:
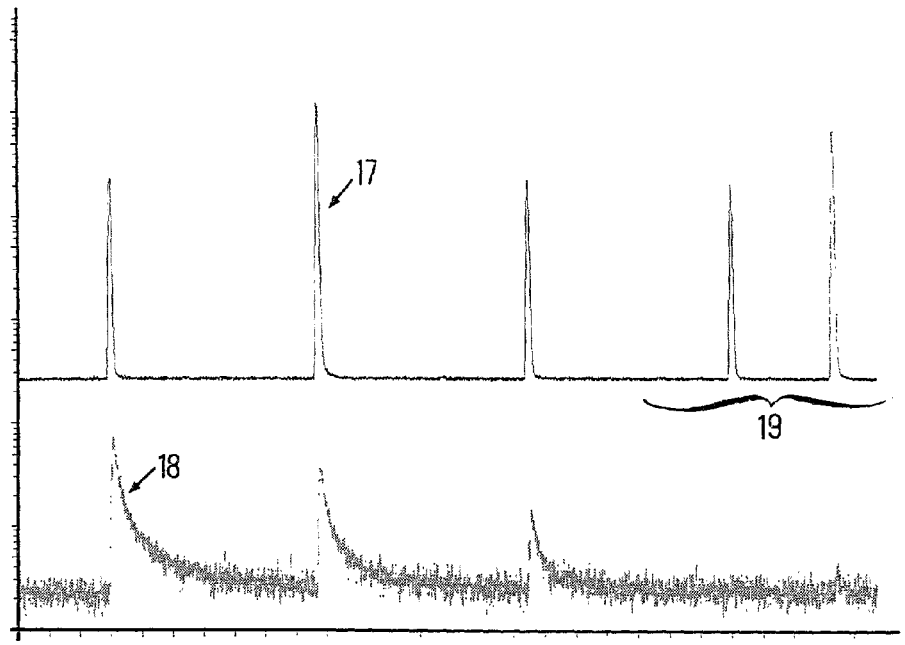

FIG. 6a corresponds to a flow rate of 93 ml/min, FIG. 6b to a flow rate of 50 ml/min.

Peaks 17 and 18 respectively correspond to C1 and C7. Zones 19 represent washing with pure C1.

Signal 18 relative to toluene is much wider and trailing in the polyethylene tube. This degradation becomes more marked as the flow rate decreases, i.e. when the transit time increases.

In comparison with the THV tube, the polyethylene tube is markedly less efficient for heavy hydrocarbon transport, even though the adsorption of toluene does not seem to be irreducible, it is clear that the displacement of toluene in a polyethylene tube causes disturbances. Furthermore, the transit time variation has an effect on the quality of the signal received during transport in the polyethylene tube, which is not the case during transport in the THV tube.

Figure 7:
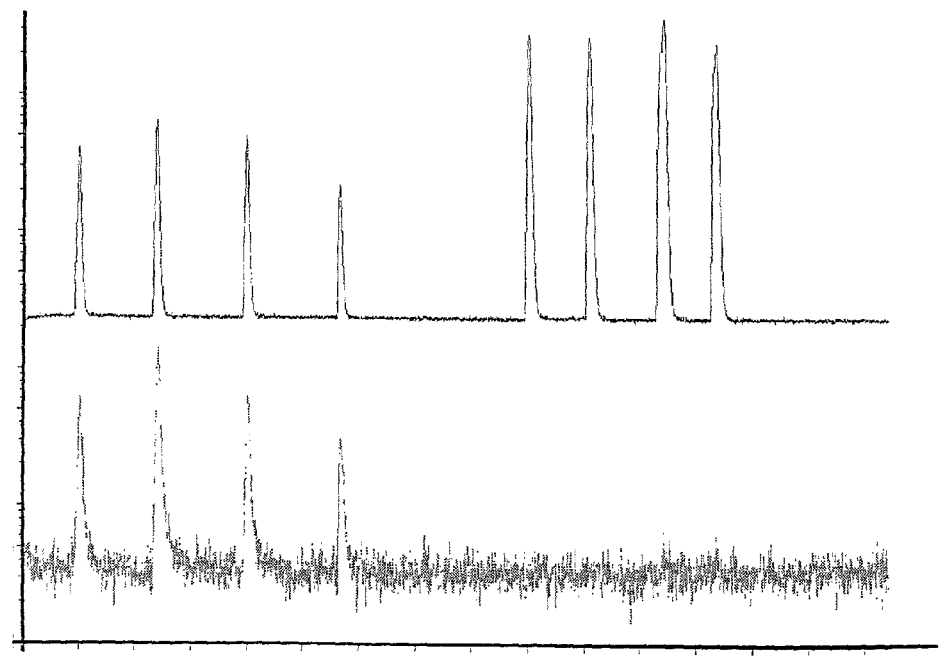

FIG. 7 shows the results obtained under low temperature conditions (2° C.). The THV line according to the assembly of FIG. 2 is placed in a refrigerating system. The C1 and C7 transport results that appear in FIG. 7 show that they are substantially similar to those obtained at ambient temperature.

Figure 12:
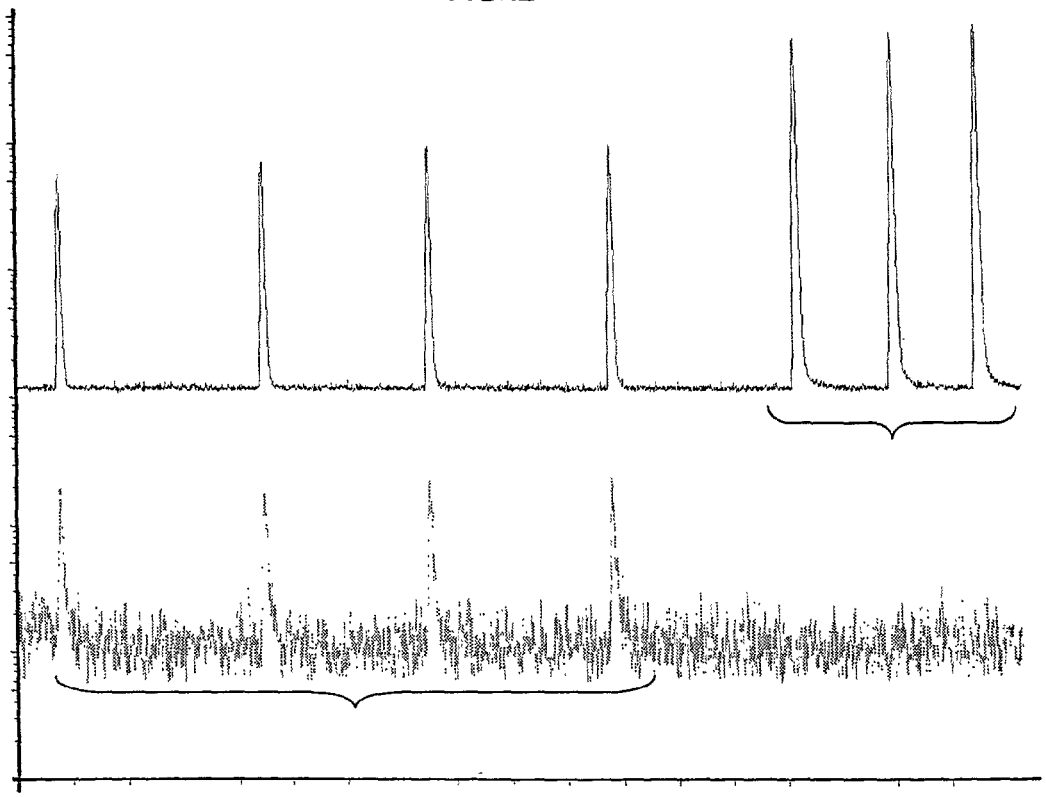
Figure 13:
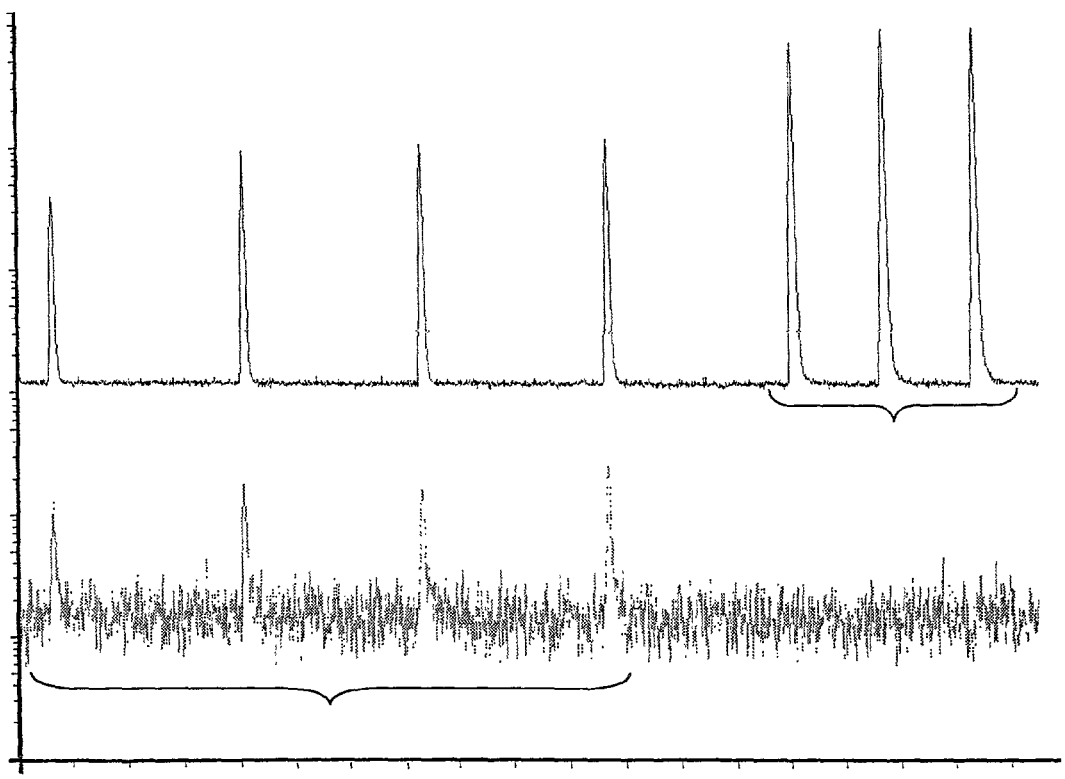

FIGS. 12 and 13 show the results of the tests carried out from the assembly of FIG. 2 in order to compare the performances of PTFE (FIG. 12) and THV (FIG. 13). The reference gas used here comprises 10% C1, 1000 ppm benzene, 500 ppm toluene, the rest being nitrogen.

The test conditions are as follows: PTFE (FIG. 12): Q=93 ml/min; Ps=20 mb; Pe=27 mb. The inside diameter of the line is 8 mm, the thickness is 1 mm, and it is 50 m long.

The test conditions are as follows: THV (FIG. 13): Q=93 ml/min; Ps=20 mb; Pe=28 mb. The inside diameter of the line is 7.3 mm, the thickness is below 0.5 mm and it is 50 m long.

The measurements are identical and thus show similar performances for PTFE and THV.

Figure 8:
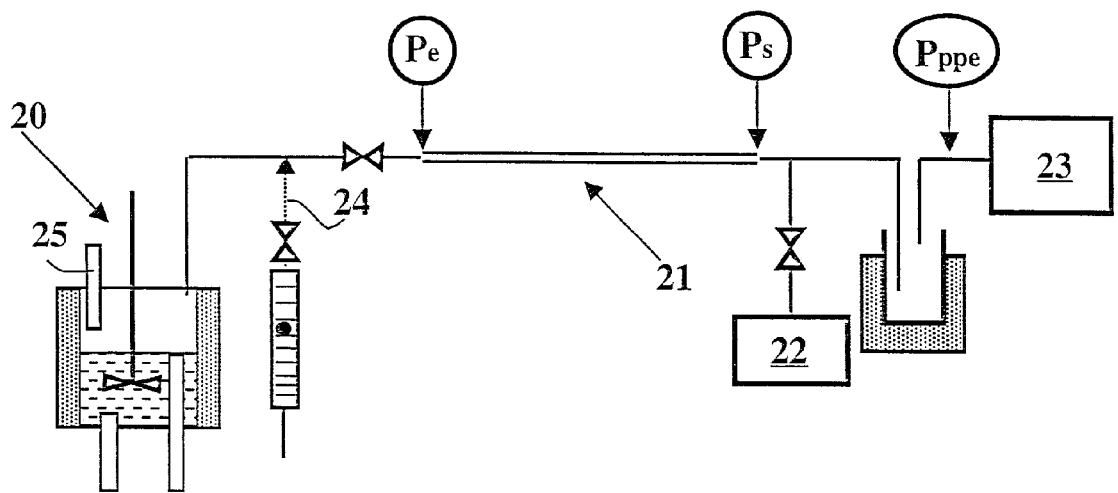

FIG. 8 shows the diagram of an extraction device 20 or degasser, a transport line 21 for the gas sampled, a measurement or analysis plant 22, a vacuum pump 23 for operating degasser 20 and line 21 under underpressure (it can be noted that all the pressure values are given in absolute pressure). Adjustment can be performed by restricting air inlet 25. Reference number 24 refers to intermittent flow rate control means. A C7/C1 gas sample can be introduced through 24 or 25. Line 21 consists of a 50-m long THV tube. The operating conditions are as follows: Pe=34 mb, Ps=20 mb and Q=93 ml/min. The gas sample can also be injected through 25 in the water filling the housing of degasser 20. Document FR-99/12,032, which describes a degasser according to FIG. 8, is mentioned by way of reference.

Figure 9:
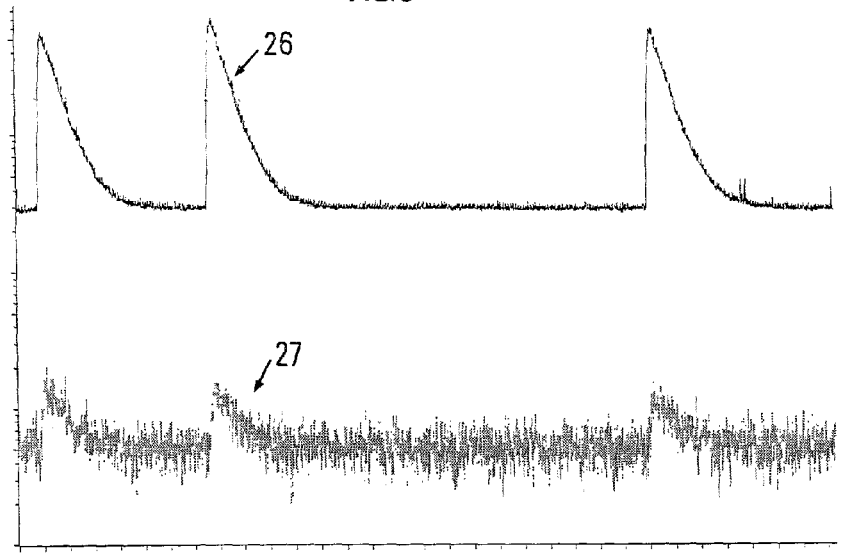

FIG. 9 shows the results of C1 (peak 26) and C7 (peak 27) measurements. It appears that, under the conditions of an industrial plant, the transport of C7 is correctly performed by means of a THV line. Injection of the sample in the liquid of the degasser or at the inlet of the line does not change the results.

Figure 10:
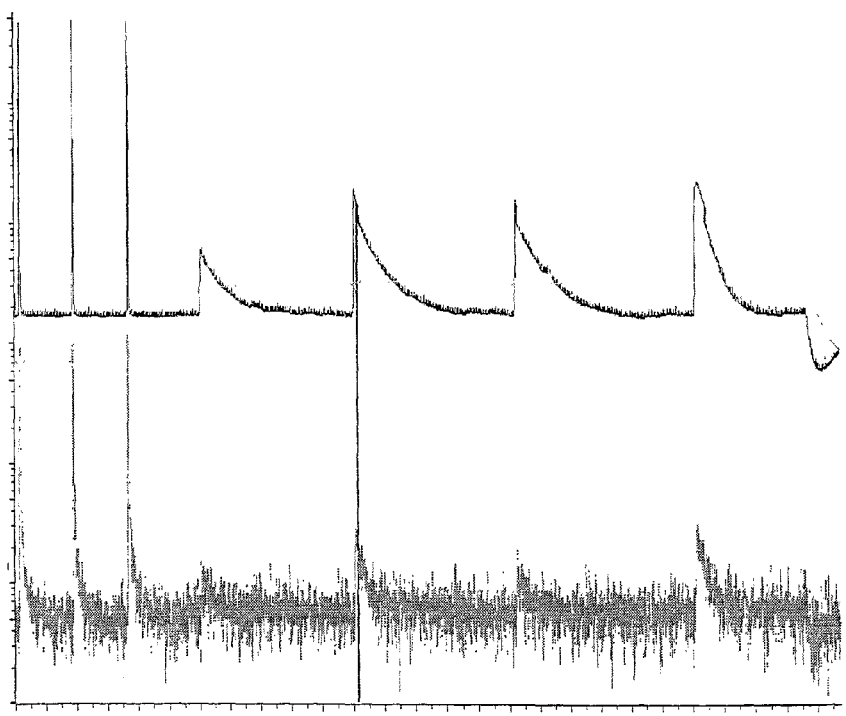

FIG. 10 gives the results of a test carried out by means of an assembly according to FIG. 8, but operated under atmospheric conditions concerning the degasser. Such a degasser is for example described in document U.S. Pat. No. 5,090,256 mentioned here by way of reference. The C1 and C7 gas sample is injected in a 1.2-density drilling mud placed in the degasser. The first three peaks correspond to the response to three successive gas injections directly at the inlet of the line, by way of comparison with the signal obtained after injection of the sample in the mud.

It can be noted that the presence of C7 is recognized by the measurement in the mass spectrometer, the transport is therefore correct in line 21 according to the invention. Under similar conditions, with a conventional polyvinyl line, C7 is not detected in the spectrometer and C1 is under evaluated.

Figure 11:
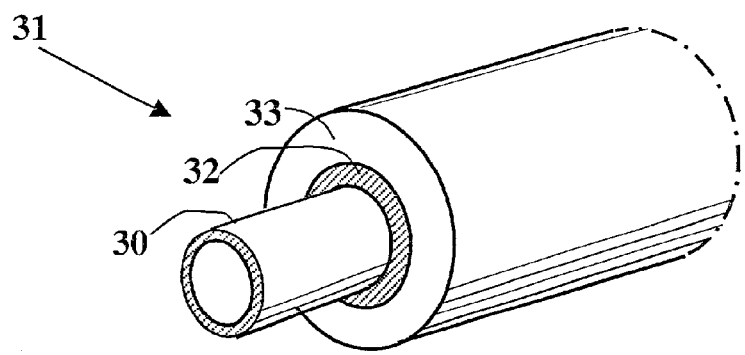
FIG. 11 illustrates a tube according to the invention.

FIG. 11 diagrammatically shows a line according to the invention where inner tube 30 is made of THV and covered with a coating 31 consisting for example of an elastomer or PE layer 33 as a mechanical protective layer, armored or not. This layer is preferably glued on tube 30 by a layer of adhesive material 32. Tube 30 can be 7.3 mm in inside diameter, with a thickness below about 0.5 mm, and preferably below 0.2 mm. The outside diameter of the whole tube is about 13 mm.

The invention claimed is:

1. An analysis and/or measuring device comprising means for extracting, in the gaseous form, hydrocarbons contained in a liquid drilling fluid after drilling in a reservoir rock, means for transporting said extracted gases, and means intended for analysis and measurement on these extracted gases, characterized in that said transport means include a tubular line comprising an inner tube which limits retention of trace hydrocarbons made from at least one plastic selected from the group consisting of PTFE (polytetrafluoroethylene), FEP (tetrafluoroethene-perluoroprene copolymer), PVDF (polyvinylidene fluoride), ETFE (tetrafluoroethylene-ethylene copolymer), ETECE (ethylene-trifluorochloroethylene copolymer), PCTFE (polychlorotrifluoroethylene), FPA (perfluoroalkoxyalkane), hexafluoropropylene/vinylidene fluoride copolymers, hexafluoropropylene/vinylidene fluoride/tetrafluoropropylene THV terpolymers, tetrafluoroethylene/hexafluoropropylene/treated vinylidene fluoride, PEEK (polyetherether ketone), PEKK, PAEK, PEK, and aliphatic polyketones.

2. A device as claimed in claim 1, wherein said inner tube is externally protected by at least one other sheath.

3. A device as claimed in claim 1, wherein the thickness of the inner tube ranges between 0.1 and 0.5 mm.

4. A device as claimed in claim 1, wherein the thickness of the inner tube ranges between 0.1 and 0.2 mm.

5. A device as claimed in claim 1, wherein the inside diameter of the inner tube ranges between 3 and 12 mm.

6. A device as claimed in claim 1, wherein the inside diameter of the inner tube ranges between 6 and 10 mm.

7. A device as claimed in claim 1, wherein said tubular line is several ten meters long.

8. A method for analysis and/or measuring comprising:
extracting, in the gaseous form, hydrocarbons contained in a liquid drilling fluid after drilling in a reservoir rock, transporting said extracted gases, and analyzing or measuring the extracted gases, wherein the extracted gases are transported in a tubular line comprising an inner tube which limits retention of trace hydrocarbons made from at least one plastic selected from the group consisting of PTFE (polytetrafluoroethylene), FEP (tetrafluoroethene-perfluoroprene copolymer), PVDF (polyvinylidene fluoride), ETFE (tetrafluoroethylene-ethylene copolymer), ETFCE (ethylene-trifluorochloroethylene copolymer), PCTFE (polychlorotrifluoroethylene), FPA (perfluoroalkoxyalkane), hexafluoropropylene/vinylidene fluoride copolymers, hexafluoropropylene/vinylidene fluoride/tetrafluoropropylene THV terpolymers, tetrafluoroethylene/hexafluoropropylene/treated vinylidene fluoride, PEEK (polyetherether ketone), PEKK, PAEK, PEK, and aliphatic polyketones.

9. A method as claimed in claim 8, wherein said inner tube is made of THV.

10. A method as claimed in claim 8, wherein said inner tube is externally protected by at least one other sheath.

11. A method as claimed in claim 8, wherein the thickness of the inner tube ranges between 0.1 and 0.5 mm.

12. A method as claimed in claim 8, wherein the thickness of the inner tube ranges between 0.1 and 0.2 mm.

13. A method as claimed in claim 8, wherein the inside diameter of the inner tube ranges between 3 and 12 mm.

14. A method as claimed in claim 8, wherein the inside diameter of the inner tube ranges between 6 and 10 mm.

15. A method as claimed in claim 8, wherein said tubular line is several ten meters long.

* * * * *